United States Patent [19]

Vogel et al.

[11] 4,341,720
[45] Jul. 27, 1982

[54] PROCESS FOR THE PREPARATION OF OXALYL CHLORIDE

[75] Inventors: Axel Vogel; Guido Steffan, both of Odenthal; Karl Mannes; Viktor Trescher, both of Leverkusen, all of Fed. Rep. of Germany

[73] Assignee: Bayer Aktiengesellschaft, Leverkusen, Fed. Rep. of Germany

[21] Appl. No.: 247,186

[22] Filed: Mar. 24, 1981

Related U.S. Application Data

[63] Continuation of Ser. No. 73,980, Sep. 10, 1979, abandoned.

[30] Foreign Application Priority Data

Sep. 16, 1978 [DE] Fed. Rep. of Germany ....... 2840435

[51] Int. Cl.³ ............................................. C07C 57/00
[52] U.S. Cl. .............................................. 260/544 Y
[58] Field of Search .................................. 260/544 Y

[56] References Cited

U.S. PATENT DOCUMENTS 1,888,713 11/1932 Britton et al. .................. 260/544 Y
1,936,739 11/1933 Townend ........................ 260/544 Y

OTHER PUBLICATIONS

Wagner & Zook, "Synth. Org. Chem.", (1965), pp. 546, 547.

*Primary Examiner*—Alan Siegel
*Attorney, Agent, or Firm*—Sprung, Horn, Kramer & Woods

[57] ABSTRACT

In a process for the preparation of oxalyl chloride from an oxalic acid compound of the formula

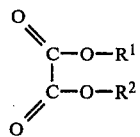

wherein $R^1$ and $R^2$ are identical or different and represent hydrogen or a lower alkyl radical, and phosphorus pentachloride in the presence of phosphorus oxychloride, the improvement wherein the reaction is carried out in the presence of an amino compound of the formula

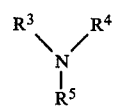

wherein $R^3$ represents alkyl, aralkyl, aryl or an acyl group, optionally substituted by amino or carboxamido and $R^4$ and $R^5$ are identical or different and represent hydrogen or alkyl, aralkyl, or aryl, optionally substituted by amino or carboxamido, or $R^4$ and $R^5$ are linked in an optionally substituted carbocyclic ring with 5 to 7 ring members, which optionally contains nitrogen, sulphur and/or oxygen and is optionally substituted by alkyl, aralkyl, aryl and/or amino groups, and $R^3$ represents hydrogen or alkyl, which can be linked with $R^4$ to form a carbocyclic ring, aralkyl or aryl, optionally substituted by an amino or carboxamido group, or optionally forms a double bond in one of the radials $R^4$ or $R^5$, and the oxalyl chloride formed is distilled off during the reaction.

20 Claims, No Drawings

PROCESS FOR THE PREPARATION OF OXALYL CHLORIDE

This is a continuation of application Ser. No. 73,980, filed Sept. 10, 1979 now abandoned.

The invention relates to a process for the preparation of oxalyl chloride from oxalic acid compounds, such as oxalic acid or oxalic acid esters, and phosphorus pentachloride in the presence of phosphorus oxychloride.

Yields of only 45 to 55% are achieved by the known processes for the preparation of oxalyl chloride from oxalic acid by reaction with phosphorus pentachloride in the presence of phosphorus oxychloride (Ber. 41, 3558–3566, German Reichspatent No. 216,918, German Reichspatent No. 216,919 and J. Am. Chem. Soc. 73, 4294–4296 (1951)). Long reaction times (18 to 72 hours) are required in the preparation of oxalyl chloride by these processes. Large amounts of phosphorus oxychloride (2.6 to 4.5 mols per mol of oxalyl chloride) and hydrogen chloride (about 4 mols per mol of oxalyl chloride), and carbon monoxide, carbon dioxide and phosgene are obtained as by-products. Furthermore, these processes present difficult safety problems as a result of the reaction which starts up abruptly and proceeds with the evolution of large amounts of gas.

A process has been found for the preparation of oxalyl chloride from oxalic acid compounds of the formula

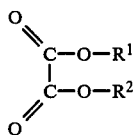

(I)

wherein
R$^1$ and R$^2$ are identical or different and represent hydrogen or a lower alkyl radical, and phosphorus pentachloride in the presence of phosphorus oxychloride, which is characterized in that the reaction is carried out in the presence of an amino compound of the formula

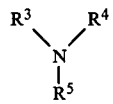

(II)

wherein
R$^3$ represents alkyl, aralkyl, aryl or an acyl group, optionally substituted by amino or carboxamido and
R$^4$ and R$^5$ are identical or different and represent hydrogen or alkyl, aralkyl, or aryl, optionally substituted by amino or carboxamido, or
R$^4$ and R$^5$ can be linked in an optionally substituted carbocyclic ring with 5 to 7 ring members, which optionally contains nitrogen, sulphur and/or oxygen and is optionally substituted by alkyl, aralkyl, aryl and/or amino groups, and
R$^3$ represents hydrogen or alkyl, which can be linked with R$^4$ to form a carbocyclic ring, aralkyl or aryl, optionally substituted by an amino or carboxamido group, or optionally forms a double bond to one of the radicals R$^4$ or R$^5$, optionally in the presence of an inert diluent, and the oxalyl chloride so formed is distilled off during the reaction.

The process according to the invention can be illustrated by the following equation:

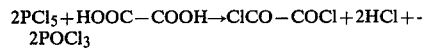

Lower alkyl radicals (R$^1$ and R$^2$) can be straight-chain or branched hydrocarbon radicals with 1 to 6, preferably 1 to 4, carbon atoms. Examples which may be mentioned are methyl, ethyl, propyl, isopropyl, butyl, isobutyl, pentyl, isopentyl, hexyl and isohexyl.

Alkyl radicals (R$^3$, R$^4$ and R$^5$) can be straight-chain or branched hydrocarbon radicals with 1 to 12, preferably 1 to 6, carbon atoms. Examples which may be mentioned are: methyl, ethyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, isoundecyl, dodecyl and isododecyl.

Aralkyl radicals (R$^3$, R$^4$ and R$^5$) can be alkyl radicals with 1–4 carbon atoms, which are substituted by an aromatic hydrocarbon radical with 6–12 carbocyclic C atoms, preferably phenyl and toluyl; for example benzyl and o-, m- and p-methylbenzyl. Aryl radicals (R$^3$, R$^4$ and R$^5$) can be aromatic hydrocarbon radicals with 6 to 12 carbocyclic carbon atom preferably phenyl and toluyl.

Acyl radicals (R$^3$) can be radicals of the formula

wherein
R$^6$ is a straight-chain or branched lower alkyl radical, preferably with 1 to 6 and particularly preferably 1 to 4, carbon atoms, or an aromatic radical, preferably a phenyl radical.

Examples of R$^6$ which may be mentioned are methyl, ethyl, propyl, isopropyl, butyl, isobutyl, pentyl, isopentyl, hexyl, isohexyl and phenyl.

The radicals R$^6$ can also be linked with one of the radicals R$^3$ or R$^4$ to form a ring, preferably with 5 or 6 ring members, which also contains, in addition to the amine nitrogen, hydrocarbon members and optionally nitrogen, sulphur and/or oxygen.

The pyrrolidonyl ring may be mentioned as an example.

The radicals R$^4$ and R$^5$ can also be linked to form an optionally substituted, carbocyclic, preferably aromatic ring (optionally containing nitrogen, sulphur and/or oxygen, in addition to the amine nitrogen), with 5 to 7, preferably 5 or 6, ring members, according to formula III. In addition to the amino nitrogen, this ring can optionally also contain 1 or 2 nitrogen, sulphur or oxygen atoms. The ring can be substituted by 1–5 alkyl, aralkyl or aryl groups and/or 1–2 amino groups.

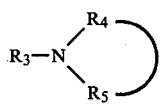

(III)

Examples of carbocyclic rings which may be mentioned are: pyrrolidine, piperidine, piperazine, triazole, pyrrole, pyrazole, imidazole, thiazole, oxazole, morpholine, pyridine, pyrimidine and triazine. These carbocyclic rings can furthermore be substituted on fused benzo rings, for example benzotriazole, benzopyrrole, benzoimidazole, benzothiazole, benzoxazole, quinoline, isoquinoline, indole and acridine.

The radicals $R^1$ to $R^6$ can be substituted by further amino groups, preferably by 1 or 2, or carboxamido groups, preferably by 1 to 2, or alkyl-, preferably by 1 to 2, aralkyl-, preferably by 1-2, or aryl-, preferably by 1. The substituents $R^1$ and $R^6$ can, of course, be substituted by further radicals which do not change under the reaction conditions.

Examples of these radicals which may be mentioned are: the halogens, preferably chlorine and bromine, nitro and sulphonyl groups. Preferred substituents which may be mentioned for the compounds of the formula (III) are the dimethylamino groups and the pyrrolidinoyl group, in particular in the para-position to the amine nitrogen, and 1-2 alkyl groups with 1-2 C atoms in the p- and o-position.

Oxalic acid compounds of the formula IV

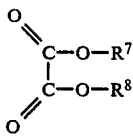

(IV)

wherein
$R^7$ and $R^8$ are identical or different and can denote hydrogen or a straight-chain or branched alkyl radical with 1 to 4 carbon atoms, are preferred for the process according to the invention.

Examples of these compounds which may be mentioned are: oxalic acid, oxalic acid dimethyl ester, oxalic acid diethyl ester, oxalic acid di-propyl ester, oxalic acid di-iso-propyl ester, oxalic acid di-n-butyl ester and oxalic acid di-iso-butyl ester. Preferred oxalic acid compounds are oxalic acid and oxalic acid dimethyl ester.

Oxalic acid compounds which can be employed for the process according to the invention can be prepared by known methods (Ullman, 3rd edition, volume 13, page 52). For example, oxalic acid is prepared from sodium formate by heating to 380° C., hydrogen being split off. The ester can be optionally subsequently prepared be reaction with an alcohol.

Preferred amino compounds for the process according to the invention are tertiary amines and carboxamides of the formula V

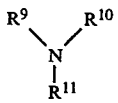

(V)

wherein
$R^9$ represents alkyl with 1 to 4 carbon atoms, aralkyl with 7 to 9 carbon atoms, phenyl or acyl with 1 to 8 carbon atoms, optionally substituted by an amino or carboxamido group, and
$R^{10}$ and $R^{11}$ are identical or different and represent alkyl with 1 to 4 carbon atoms, aralkyl with 7 to 9 carbon atoms and phenyl, optionally substituted by amino or carboxamido, or
$R^{10}$ and $R^{11}$ can be linked in a 5-membered or 6-membered ring, which optionally also contains a nitrogen, sulphur or oxygen atom as a further heteroatom and is optionally substituted by 1-5 alkyl groups with 1-4 carbon atoms, a fused-on, optionally further substituted benzene ring or 1-2 dialkylamino or carbocyclic alkylideneamino groups with 1-4 carbon atoms in each case, and
$R^9$ represents hydrogen or alkyl with 1 to 4 carbon atoms, which can be linked with $R^{10}$ to form a carbocyclic ring, aralkyl with 7 to 9 carbon atoms, phenyl or acyl with 1 to 8 carbon atoms, optionally substituted by an amino or carboxamido group, or optionally forms a double bond to one of the radicals $R^{10}$ or $R^{11}$.

Examples which may be mentioned of amino compounds for the process according to the invention are primary, secondary and tertiary amines and carboxylic acid amides.

The following amino compounds may particularly preferably be mentioned:
(a) tertiary amines of the formula

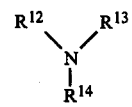

VI wherein
$R^{12}$, $R^{13}$ and $R^{14}$ are identical or different and represent optionally substituted alkyl with 1 to 4 carbon atoms, aralkyl with 7 to 9 carbon atoms or phenyl,
(b) carboxamides of the formula

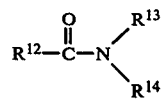

VII wherein
$R^{12}$, $R^{13}$ and $R^{14}$ have the abovementioned meaning, and
(c) heterocyclic amines of the formula

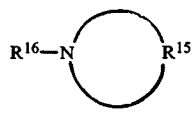

wherein
$R^{15}$ is an optionally substituted 4- or 5-membered chain consisting of hydrocarbon members and optionally also containing a further nitrogen, oxygen or sulphur atom and
$R^{16}$ represents hydrogen, optionally substituted alkyl with 1 to 4 carbon atoms, which can be linked with $R^{15}$ to form a carbocyclic ring, aralkyl with 7 to 9 carbon atoms or phenyl, or forms a double bond in the aromatic system.

Examples of amines which may be mentioned are: methylamine, dimethylamine, trimethylamine, ethylamine, diethylamine, triethylamine, propylamine, dipropylamine, tributylamine, N,N-dimethylaniline, N,N-diethylaniline, N,N-dipropylaniline, N,N-dialkyltoluidines, tribenzylamine, N,N-dimethylbenzylamine, N,N-diethylbenzylamine, ethylenediamine, N,N-dimethylethylenediamine, N,N'-dimethylethylenediamine, N,N,N',N'-tetramethylethylenediamine, propylenediamine, dimethylpropylenediamine, tetramethylpropylenediamine, diethylenetriamine, N,N',N''-trimethyldiethylenetriamine, permethyldiethylenetriamine, N,N-dimethylneopentanediamine, N,N,N',N'-tetramethyl-neopentanediamine, pyrrolidine, 1-methylpyrrolidine, piperidine, 1-methylpiperidine, 1-ethylpiperidine, 1,2-dimethylpiperidine, piperazine, 1-methylpiperazine, 1,4-dimethylpiperazine, 1,2,4,5-tetramethylpiperazine, 1,4,5,6-tetrahydro-1,2-dimethylpyrimidine, 1,4-diazabicyclo-[2,2,2]octane, 1,5-diazabicyclo-[4,3,0]-non-5-ene, 1,8-diazabicyclo-[5,4,0]-undec-7-ene, quinnuclidine, 1,3,5-trimethylhexahydro-s-triazine, hexamethyl-hexahydro-s-triazine, 1-methyl-1,2,4-triazole, 1-methylpyrrole, 1-methyl-pyrazole, 1-methylimidazole, 1,2-dimethyl-imidazole, 1-methyl-benzimidazole, 1-methyl-benzotriazole, thiazole, 4,5-dimethylthiazole, benzothiazole, oxazole, 2-methyloxazole, 4,5-dimethyloxazole, benzoxazole, 2-methylbenzoxazole, morpholine, 4-methylmorpholine, 4-phenylmorpholine, 4,4'-(1,2-ethanediyl)-bis-morpholine, pyridine, 2-methylpyridine, 3-methylpyridine, 4-methylpyridine, 2-ethylpyridine, 3-ethylpyridine, 4-ethylpyridine, 2,4-dimethylpyridine, 2,5-dimethylpyridine, 2,6-dimethylpyridine, 2-ethyl-3-methylpyridine, 2-ethyl-4-methylpyridine, 2-ethyl-5-methylpyridine, 2-ethyl-6-methylpyridine, 4-ethyl-2-methylpyridine, 4-ethyl-3-methylpyridine, 3-ethyl-5-methylpyridine, 3-ethyl-6-methylpyridine, 2,4,6-trimethylpyridine and isomers, 4-dimethylamino-pyridine, 4-pyrrolidinopyridine, 2,2'-dipyridine, quinoxaline, pyrimidine, methyl-pyrimidines, dimethylpyrimidines, triazine, phenyltriazine, trimethyltriazine, thiazine, 1-methyl-indole, quinoline, isoquinoline, 2-methylquinoline, 4-methylquinoline, 6-methylquinoline, 1-methylisoquinoline, 1-methyl-1,2,3,4-tetrahydroquinoline, acridine, hexahydrotriamines, pyrrole, pyrazole, imidazole and triazole.

Preferred amines are trimethylamine, triethylamine, pyridine, 2-methylpyridine, 4-methylpyridine, 4-ethylpyridine, 2,4-dimethylpyridine, 1,5-diazabicyclo-[4,3,0]-non-5-ene, 1,8-diazabicyclo-[5,4,0]-undec-7-ene, dimethylpiperazine, quinoline and isoquinoline.

Examples of acid amides which may be mentioned are formamide, N,N-dimethylformamide, acetamide, N,N-dimethylacetamide, N,N-dimethylpropionamide, N,N-dimethylbenzamide and N-methylpyrrolidinone. Preferred acid amides are N,N-dimethylformamide and N,N-dimethylacetamide.

The amines for the process according to the invention can be prepared by known methods, for example by alkylating ammonia, pyridine or other heterocyclic amines, which are preferably isolated from natural products, in particular coal tar, with alkyl halides.

The carboxylic acid amides for the process according to the invention can be prepared by known methods, for example by reacting carboxylic acid chlorides with ammonia or primary or secondary amines.

For the process according to the invention, it is, of course, possible to employ a mixture of various amino compounds.

The forms in which the amines and carboxylic acid amides are employed for the process according to the invention can be varied as desired. In general, the substances are employed in the pure form, or as hydrochlorides or aqueous solutions. If aqueous solutions are used, the consumption of phosphorus pentachloride by reaction with the water introduced must appropriately be taken into consideration.

It is possible to employ phosphorus pentachloride either in the pure form or in the technical form for the process according to the invention. For example, phosphorus pentachloride which is obtained by reacting phosphorus trichloride with chlorine can be employed. (Ullmann, 3rd edition, volume 13, page 562).

In general, the amino compounds are employed in amounts of 0.001 to 0.5 part by weight, preferably 0.005 to 0.1 part by weight and particularly preferably 0.01 to 0.05 part by weight, per part by weight of phosphorus pentachloride.

In general, the reaction of oxalic acid and oxalic acid esters with phosphorus pentachloride by the process according to the invention is carried out in the presence of phosphorus oxychloride and if appropriate further inert diluents, such as, for example, methylene chloride, chloroform, carbon tetrachloride, 1,2-dichloroethane, 1,1,2,2-tetrachloroethane or 1,2-dibromoethane. In general, 0.1–20 parts by weight, preferably 0.2–10 parts by weight and particularly preferably 0.3–2 parts by weight, are used per part by weight of phosphorus pentachloride. The reaction is preferably carried out in the presence of phosphorus oxychloride.

In general, the reaction of oxalic acid and oxalic acid esters with phosphorus pentachloride by the process according to the invention is carried out in the temperature range from 10° to 115° C., preferably in the temperature range from 20° to 100° C. and in particular in the temperature range from 40° to 80° C. In general, the reaction is carried out under a pressure of 0.02 to 2 bars, preferably 0.1 to 1 bar and particularly preferably 0.15 to 0.5 bar.

The oxalic acid and oxalic acid esters are employed in bulk or as a suspension or solution in phosphorus oxychloride, if appropriate in the other inert, abovementioned diluents. Oxalic acid is preferably employed in bulk or as a suspension in phosphorus oxychloride, in a concentration of up to 1.5 parts by weight of oxalic acid per part by weight of phosphorus oxychloride.

2 mols of phosphorus pentachloride are required for stoichiometric conversion of oxalic acid or oxalic acid esters to oxalyl chloride. However, in the process according to the invention, it is advantageous to employ phosphorus pentachloride in an excess of up to 20 mols, preferably up to 10 mols and particularly preferably up to 6 mols, per mol of oxalic acid or oxalic acid ester. In general, the unreacted phosphorus pentachloride is left in the reactor in the case of a continuous procedure or used for a further reaction in the case of a discontinuous procedure, so that no loss of phosphorus pentachloride occurs. The consumption of phosphorus pentachloride is then at least 1.7 mols, preferably 1.8 to 2.0 mols, per mol of oxalic acid.

The phosphorus pentachloride can be employed as a solid or as a solution or suspension in phosphorus oxychloride or an inert diluent. In general, phosphorus pentachloride is prepared by known methods (Ullman, 3rd edition, volume 13, page 562) by reacting phosphorus trichloride with chlorine.

In a preferred embodiment of the process according to the invention, the phosphorus pentachloride is first prepared, and the oxalyl chloride is then prepared in the same reaction medium in a so-called one-pot reaction. Surprisingly, preparation of phosphorus pentachloride from phosphorus trichloride and chlorine can also be effected in the presence of the amines and/or carboxylic acid amides employed in the process according to the invention without the catalytic activity of these compounds being lost because of the reaction conditions of the phosphorus trichloride chlorination. The reaction of phosphorus trichloride with chlorine to give phosphorus pentachloride is carried out in the presence of phosphorus oxychloride and if appropriate inert diluents, and in the presence of the amines and/or carboxamides used according to the invention. In general, the reaction is carried out in the temperature range from 0° to 130° C., preferably in the temperature range from 20° to 110° C. and particularly preferably in the temperature range from 40° to 90° C. In general, the pressure is 0.02 to 2 bars, preferably 0.1 to 1.5 bars and particularly preferably 0.15 to 1 bar. The amount of phosphorus oxychloride and, if appropriate, inert diluent, is in general 0.1 to 20 parts by weight, preferably 0.2 to 10 parts by weight and particularly preferably 0.3 to 2 parts by weight, of phosphorus oxychloride and, if appropriate, inert diluent, per part by weight of phosphorus pentachloride produced. In general, the chlorine required for the reaction is employed in an amount of at least 0.95 mol. preferably 1 to 1.1 mols, per mol of phosphorus trichloride.

In the reaction according to the invention, of oxalic acid compounds with phosphorus pentachloride in the presence of amino compounds, the oxalyl chloride formed is distilled off during the reaction. The oxalyl chloride is preferably distilled as a mixture with phosphorus oxychloride, the amount of phosphorus oxychloride also distilled being adjusted to within the range of 0–20 parts by weight, preferably 2–10 parts by weight, of phosphorus oxychloride per part by weight of oxalyl chloride.

In the preferred embodiment of the process according to the invention, phosphorus oxychloride is distilled off with the oxalyl chloride to the extent such that in the case of several successive batches in the discontinuous procedure or in the case of a continuous procedure, the amount of phosphorus oxychloride first initially introduced is kept approximately constant in the reactor.

The process according to the invention can be carried out, for example, as follows:

Phosphorus pentachloride is initially introduced into the reaction vessel in phosphorus oxychloride and if appropriate in an inert diluent, and the oxalic acid compound, if appropriate in phosphorus oxychloride and if appropriate in a diluent, is then added. The temperature conditions and pressure conditions are advantageously chosen so that the oxalyl chloride formed is distilled off as a mixture with phosphorus oxychloride during the reaction. The oxalyl chloride is then isolated from the distillate by rectification.

If, in the preferred embodiment of the process according to the invention, the preparation of the phosphorus pentachloride is combined with the preparation of the oxalyl chloride in a one-pot process, phosphorus pentachloride is first prepared by reacting phosphorus trichloride with chlorine, preferably in phosphorus oxychloride as a solvent, in the presence of an amino compound according to the formula II. The oxalic acid compound can then be added, without further working up, and the oxalyl chloride can be prepared according to the invention.

Oxalyl chloride is advantageously obtained in high yields and high purity by the process according to the invention. The process presents no particular safety problems.

It is surprising that the yield of oxalyl chloride can be improved by the procedure according to the invention, although the formation of oxalyl chloride takes place via the stage of the extremely unstable oxalic acid monochloride, the isolation of which has not been successful even at extremely low temperatures and which decomposes irreversibly to carbon monoxide, carbon dioxide and hydrochloric acid very rapidly (Ber. 46, 1426). The yields hitherto obtained were thus only at most 55% of theory (Ber. 41, 3558 and J. Amer. Chem. Soc. 73, 4294). On the other hand, yields of up to 95% of theory are achieved by the process according to the invention.

At the same time, the amount of by-products obtained is reduced almost down to the stoichiometric amount of hydrochloric acid. Oxalyl chloride is an intermediate product for polyamides and polyesters (U.S. Pat. No. 2,816,141).

EXAMPLE 1

1,000 g of phosphorus pentachloride and 12 g of triethylamine are suspended in 500 g of phosphorus oxychloride in a 2 l four-necked flask with a stirrer, solids metering funnel and distillation attachment. 100 g of anhydrous oxalic acid are introduced at a reaction temperature of 60° C. and under an operating pressure of 250 mbars in the course of 40 minutes. Finally, the mixture is subsequently stirred at 70° C. and under 250 mbars for 30 minutes. During the metering time and subsequent stirring time, 497 g of a mixture containing 20.7% by weight of oxalyl chloride and 78.4% by weight of phosphorus oxychloride are obtained in the distillation receiver. A mixture which contains 588 g of unreacted phosphorus pentachloride, the amount of triethylamine employed and residual phosphorus oxychloride remains in the reactor.

The yield is 73% of theory, relative to oxalic acid, or 82% of theory, relative to phosphorus pentachloride.

EXAMPLE 2

412 g of phosphorus pentachloride and 75 g of phosphorus oxychloride are subsequently added to the mixture according to Example 1 remaining in the reactor. 100 g of anhydrous oxalic acid are then added at a reaction temperature of 60° C. and under an operating pressure of 250 mbars in the course of 40 minutes and the mixture is subsequently stirred at 70° C./250 mbars for 30 minutes.

The yield in the distillation receiver is 513 g of a product containing 20.3% by weight of oxalyl chloride, corresponding to a yield of 74% of theory, relative to oxalic acid, or 83% of theory, relative to phosphorus pentachloride.

The mixture remaining in the reactor contains 588 g of unreacted phosphorus pentachloride, in addition to the triethylamine employed, and, after adding phosphorus pentachloride and phosphorus oxychloride, can be used again, as described above, for the reaction with oxalic acid.

EXAMPLE 3

1,000 g of phosphorus pentachloride, 12 g of triethylamine and 500 g of phosphorus oxychloride are initially introduced into an apparatus according to Example 1 at 75°0 C. 100 g of oxalic acid are added at an operating pressure of 375 mbars in the course of 50 minutes, whilst stirring, and the mixture is subsequently stirred at 80° C./375 mbars for 30 minutes.

The yield is 519 g of a product containing 19.0% by weight of oxalyl chloride, corresponding to 70% of theory, relative to oxalic acid.

EXAMPLES 4-16

According to Table 1, 1,000 g of phosphorus pentachloride, (a) g of the amine mentioned under (b) and 500 g of phosphorus oxychloride are initially introduced into an apparatus according to Example 1 at a temperature of (c) °C. and under an operating pressure of (d) mbars. 100 g of anhydrous oxalic acid are added in the course of (e) minutes whilst stirring, and the mixture is subsequently stirred at a temperature of (f) °C. and under a pressure of (d) mbars for 30 minutes.

The yield is (g) g of oxalyl chloride, mixed with predominantly phosphorus oxychloride. The molar yield is (b) % of theory, relative to oxalic acid.

| Example No. | a | b | °C. c | mbars d | minutes e | °C. f | g g | % h |
|---|---|---|---|---|---|---|---|---|
| 4 | 6 | 4-Ethylpyridine | 65 | 255 | 40 | 70 | 108 | 77 |
| 5 | 24 | 4-Ethylpyridine | 58 | 250 | 35 | 65 | 122 | 86 |
| 6 | 13 | Bis-(2-dimethylamino-ethyl)-methylamine | 70 | 260 | 40 | 75 | 89 | 63 |
| 7 | 20 | 4-Methylpyridine | 60 | 250 | 40 | 70 | 123 | 87 |
| 8 | 6 | 2,4-Dimethylpyridine | 60 | 250 | 30 | 70 | 120 | 85 |
| 9 | 35 | 2,4-Dimethylpyridine | 60 | 250 | 30 | 70 | 128 | 91 |
| 10 | 4 | Dimethylformamide | 60 | 250 | 30 | 70 | 115 | 82 |
| 11 | 6 | 1,4-Diazabicyclo-[2,2,2]-octane | 60 | 250 | 30 | 70 | 87 | 62 |
| 12 | 6 | 1,4-Dimethylpiperazine | 60 | 250 | 35 | 70 | 99 | 70 |
| 13 | 7 | 1,5-Diazabicyclo-[4,3,0]-non-5-ene | 60 | 250 | 35 | 70 | 112 | 79 |
| 14 | 7 | Quinoline | 60 | 250 | 40 | 70 | 98 | 69 |
| 15 | 7 | Isoquinoline | 60 | 250 | 40 | 70 | 99 | 70 |
| 16 | 7 | N,N,2,2-Tetramethyl-propane-1,3-diamine | 60 | 250 | 45 | 70 | 99 | 70 |
| 17 | 12 | Triethylamine | 45 | 150 | 40 | 50 | 98 | 70 |

EXAMPLE 18

A mixture of 2,000 parts of phosphorus pentachloride and 49 parts of 2,4-dimethylpyridine in 1,000 parts of phosphorus oxychloride are initially introduced at 60°0 C. into the reactor of a continuously operating apparatus consisting of a stirred kettle reactor with a distillation attachment and measuring and metering equipment for oxalic acid/phosphorus oxychloride mixtures and phosphorus pentachloride/phosphorus oxychloride mixtures. A suspension of 307 parts of phosphorus pentachloride in 307 parts of phosphorus oxychloride per hour, from a stirred measuring stock vessel, and a suspension of 70 parts of anhydrous oxalic acid in 70 parts of phosphorus oxychloride per hour, from a second measuring stock vessel, are metered into the reactor under an operating pressure of 250 mbars. 380 Parts per hour of a mixture containing 23.5% by weight of oxalyl chloride and 75.5% by weight of phosphorus oxychloride distil off over the distillation attachment. The oxalyl chloride is isolated from the distillate by fractional distillation over a column. The yield is 89 parts of oxalyl chloride per hour.

EXAMPLE 19

1,340 g of phosphorus oxychloride, 65 g of 2,4-dimethylpyridine and 1,769 g of phosphorus trichloride are initially introduced into a 4 l four-necked flask with stirrer, gas inlet tube and distillation attachment. 930 g of chlorine are then passed in at a bottom temperature of 85° C. in the course of 6 hours. The phosphorus pentachloride suspension formed is subjected to incipient distillation in vacuo until the excess of chlorine has been removed, and is cooled to 60° C., and a suspension of 375 g of oxalic acid in 375 g of phosphorus oxychloride is added at a reaction temperature of 60° C. and under an operating pressure of 250 mbars in the course of 4 hours. Finally, the mixture is subsequently stirred at 70° C./250 mbars for ½ an hour. During the metering in of oxalic acid and the subsequent stirring time, 2,052 g of crude distillate containing 21.9% by weight of oxalyl chloride are obtained downstream from the distillation attachment. 445 g of oxalyl chloride are isolated from this distillate by fractional distillation.

EXAMPLE 20

1,025 g of phosphorus trichloride are added to the suspension according to Example 19 remaining in the reactor and chlorination is then carried out by passing 570 g of chlorine in, at a bottom temperature of 85° C. and under reflux conditions, in the course of 3 hours. After incipient distillation, a suspension of 375 g of oxalic acid in 375 g of phosphorus oxychloride is added at a reaction temperature of 60° C. and under an operating pressure of 250 mbars in the course of 4 hours. The yield of crude distillate is 2,052 g, containing 21.9% by weight of oxalyl chloride, from which 445 g of oxalyl chloride are isolated by rectification.

EXAMPLE 21

1,500 g of phosphorus oxychloride, 100 g of 2,4-dimethylpyridine and 1,980 g of phosphorus trichloride are initially introduced in an apparatus according to Example 19. 1,040 g of chlorine are then passed in over a period of about 2 hours, the mixture being allowed to boil under reflux at a bottom temperature of about 124° C. The excess chlorine is distilled off, the mixture is cooled to 60° C. and 420 g of anhydrous oxalic acid are introduced at a reaction temperature of 60° C. and under an operating pressure of 240 mbars in the course of 4 hours, whilst stirring. 1,813 g of crude distillate containing 26.8% by weight of oxalyl chloride are isolated, from which 481 g of oxalyl chloride can be obtained by rectification.

After adding 1,215 g of phosphorous trichloride, the suspension remaining in the reactor can be treated with 640 g of chlorine at the boiling point in the same manner, and oxalic acid is then added, as previously, at 60° C./240 mbars.

What is claimed is:
1. In a process for the preparation of oxalyl chloride from an oxalic acid compound of the formula

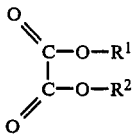

wherein R[1] and R[2] are identical or different and represent hydrogen or a lower alkyl radical, and phosphorus pentachloride in the presence of phosphorus oxychloride, the improvement wherein the reaction is carried out in the presence of 0.001 to 0.5 part by weight per part by weight of phosphorus pentachloride of pyridine or an amino compound of the formula

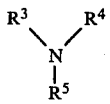

wherein

R[3] represents alkyl, aralkyl, aryl or an acyl group, optionally substituted by amino or carboxamido and R[4] and R[5] are identical or different and represent hydrogen or alkyl, aralkyl, or aryl, optionally substituted by amino or carboxamido, or R[4] and R[5] are linked in an optionally substituted carbocyclic ring with 5 to 7 ring members, which optionally contains nitrogen, sulphur and/or oxygen and is optionally substituted by alkyl, aralkyl, aryl and/or amino groups, and R[3] represents hydrogen or alkyl, which can be linked with R[4] to form a carbocyclic ring, aralkyl or aryl, optionally substituted by an amino or carboxamido group, or optionally forms a double bond in one of the radials R[4] or R[5], and the oxalyl chloride formed is distilled off during the reaction.

2. A process according to claim 1 wherein an amino compound is employed and said amino compound is one of the formula

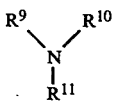

wherein

R[9] represents alkyl with 1 to 4 carbon atoms, aralkyl with 7 to 9 carbon atoms, phenyl or acyl with 1 to 8 carbon atoms, optionally substituted by an amino or carboxamido group, and R[10] and R[11] are identical or different and represent alkyl with 1 to 4 carbon atoms, aralkyl with 7 to 9 carbon atoms and phenyl, optionally substituted by amino- or carboxamido, or R[10] and R[11] can be linked in a 5-member or 6-membered ring, which optionally also contains a nitrogen, sulfur or oxygen atom as a further hetero-atom and optionally substituted by 1-5 alkyl groups with 1-4 carbon atoms, a fused-on, optionally further substituterd benzo ring or 1-2 dialkylamino or carbocyclic alkylideneamino groups with 1-4 carbon atoms in each case, and R[9] represents hydrogen or alkyl with 1 to 4 carbon atoms, which can be linked with R[10] to form a carbocyclic ring, aralkyl with 7 to 9 carbon atoms phenyl or acyl with 1 to 8 carbon atoms.

3. A process according to claim 1 carried out in the presence of an inert diluent.

4. A process according to claim 1 carried out at a temperature in the range of 10° to 115° C.

5. A process according to claim 1 carried out in the pressure range from 0.02 to 2 bars.

6. A process according to claim 1 wherein an excess of phosphorus pentachloride of up to 20 mols is reacted with the oxalic acid compound.

7. A process according to claim 1 wherein the phosphorus pentachloride is prepared by reacting phosphorus trichloride with chlorine in the presence of phosphosus oxychloride and in the presence of the amino compound.

8. A process according to claim 7 wherein the phosphorus pentachloride is prepared in the presence of an inert diluent.

9. A process according to claim 1, wherein pyridine or an amino compound of the group consisting of trimethylamine, triethylamine, 2-methylpyridine, 4-methylpyridine, 4-ethylpyridine, 2,4-dimethylpyridine, 1,4-diazabicyclo-[4,3,0]-non-5-ene, 1,8-diazabicyclo-[5,4,0]-undec-7-ene, dimethylpiperazine, quinoline and isoquinoline is employed.

10. A process according to claim 1, wherein pyridine or said amino compound is employed in amount of 0.005 to 0.1 part by weight per part by weight of said phosphorus pentachloride.

11. A process according to claim 1, wherein said pyridine or said amino compound is present in an amount of at least 0.01 part by weight.

12. A process according to claim 11, wherein said pyridine or said amino compound is present in an amount of 0.01 to 0.05 part by weight per part by weight of phosphorus pentachloride.

13. A process according to claim 1 wherein the phosphorus oxychloride is present in an amount of 0.1 to 20 parts by weight per part by weight of phosphorus pentachloride.

14. A process according to claim 1 wherein at least 6 mols of phosphorus pentachloride are employed per mol of oxalic acid compound.

15. A process according to claim 1 wherein at least 10 mols of phosphorus pentachloride are employed per mol of oxalic acid compound.

16. A process according to claim 1 wherein at least 20 mols of phosphorus pentachloride are employed per mol of oxalic acid compound.

17. A process according to claim 1 wherein the oxalyl chloride formed is distilled off during the reaction.

18. A process according to claim 17 wherein the process is conducted at a pressure of 0.15 to 1 bar.

19. A process according to claim 1 wherein the process is conducted at a pressure of 0.02 to 2 bars.

20. A process according to claim 11 wherein at least 6 mols of phosphorus pentachloride are employed per mol of oxalic acid compound.

* * * * *

UNITED STATES PATENT AND TRADEMARK OFFICE
CERTIFICATE OF CORRECTION

PATENT NO. : 4,341,720
DATED : July 27, 1982
INVENTOR(S) : AXEL VOGEL et al

It is certified that error appears in the above—identified patent and that said Letters Patent is hereby corrected as shown below:

| Col. | Line | |
|---|---|---|
| 9 | 14 | change "(b)" to --(h)--. |
| 9 | 36 | after "60°" delete "0". |
| 11 | 39, 40, 41 | (Amend. 2/4/82, page 1, line 20) after "$R^5$" change "," to --.-- and delete balance of claim. |
| 12 | 6 | (Amend. 3/20/81, page 4, line 12) after "atoms" change "." to --,-- and add --optionally substituted by an amino or carboxamino group, or optionally forms a double bond to one of the radicals $R^{10}$ or $R^{11}$.-- |
| 2 | 28 | change "atom" to --atoms--. |

Signed and Sealed this

Eighteenth Day of January 1983

[SEAL]

Attest:

GERALD J. MOSSINGHOFF

Attesting Officer    Commissioner of Patents and Trademarks